(12) United States Patent
Kansas et al.

(10) Patent No.: US 10,722,367 B2
(45) Date of Patent: Jul. 28, 2020

(54) EXPANDABLE PENILE PROSTHESIS

(71) Applicant: Bryan T. Kansas, Austin, TX (US)

(72) Inventors: Bryan T. Kansas, Austin, TX (US); Curtis N. Crane, Austin, TX (US)

(73) Assignee: Bryan T. Kansas, Austin, TX (US)

( * ) Notice: Subject to any disclaimer, the term of this patent is extended or adjusted under 35 U.S.C. 154(b) by 0 days.

(21) Appl. No.: 16/670,009

(22) Filed: Oct. 31, 2019

(65) Prior Publication Data

US 2020/0129295 A1    Apr. 30, 2020

Related U.S. Application Data

(60) Provisional application No. 62/753,128, filed on Oct. 31, 2018.

(51) Int. Cl.
| | | |
|---|---|---|
| *A61F 5/00* | (2006.01) | |
| *A61F 2/26* | (2006.01) | |
| *A61L 27/24* | (2006.01) | |
| *A61L 27/22* | (2006.01) | |
| *A61L 27/52* | (2006.01) | |

(52) U.S. Cl.
CPC ........ *A61F 2/26* (2013.01); *A61F 2220/0008* (2013.01); *A61F 2230/0008* (2013.01); *A61L 27/225* (2013.01); *A61L 27/24* (2013.01); *A61L 27/52* (2013.01)

(58) Field of Classification Search
CPC .... A61F 2/26; A61F 2/004; A61F 5/41; A61F 2005/415
USPC ...................................... 600/38–41
See application file for complete search history.

(56) References Cited

U.S. PATENT DOCUMENTS

| | | | |
|---|---|---|---|
| 6,340,362 B1 | 1/2002 | Pierer et al. | |
| 6,475,137 B1 | 11/2002 | Elist | |
| 7,637,861 B2 | 12/2009 | Kuyava et al. | |
| 7,914,439 B2 | 3/2011 | Kuyava et al. | |
| 10,398,558 B2 * | 9/2019 | Crabb | ........................ A61F 2/26 |
| 2018/0098855 A1 | 4/2018 | Crabb | |
| 2018/0200060 A1 | 7/2018 | Gomez-Llorens | |

FOREIGN PATENT DOCUMENTS

WO    WO2006096001    9/2006

OTHER PUBLICATIONS

Mona Ascha, et al., "Outcomes of Single Stage Phalloplasty by Pedicled Anterolateral Thigh Flap versus Radial Forearm Free Flap in Gender Confirming Surgery," Jul. 25, 2017, 9 pages.
Wikipedia, "Blausen 0723 Pelvis," Sep. 20, 2018, 2 pages.
Jorgensen Labs, "Cuttable Bone Plate," Sep. 20, 2018, 9 pages.
Math Is Fun, "Ellipse," Sep. 18, 2018, 6 pages.
AMS 700 LGX, "AMS 700 Penile Implant," Sep. 18, 2018, 5 pages.
Abbott, "Graftmaster RX Coronary Stent Graft System," Sep. 18, 2018, 6 pages.

(Continued)

*Primary Examiner* — John P Lacyk
(74) *Attorney, Agent, or Firm* — Trop, Pruner & Hu, P.C.

(57) ABSTRACT

An embodiment includes a penile prosthetic comprising: an expandable conduit; a pump; a reservoir; a first conduit that couples the expandable conduit to the pump; a second conduit that couples the reservoir to the pump; and a plate that couples to the expandable conduit, wherein the plate includes a concave surface. Other embodiments are described herein.

20 Claims, 8 Drawing Sheets

(56) References Cited

OTHER PUBLICATIONS

Bard Peripheral Vascular, "Impra ePTFE Vascular Grafts, Instructions for Use," May 2014, 44 pages.
The Canadian Veterinary Journal, "Orthopedic Hardware and Equipment for the Beginner: Part 2: Plates and Screws," Sep. 20, 2018, 4 pages.
Orthopedic Hardware, "UW Radiology, Orthopedic Hardware," Sep. 20, 2018, 37 pages.
Mayo Clinic, "Penile Implants," 1998-2018, 8 pages.
Wikipedia, "Phalloplasty," Jun. 20, 2018, 9 pages.
Brownstein & Crane Surgical Services, "FTM Phalloplasty Surgery," Sep. 18, 2018, 2 pages.
Wikipedia, "Pubic Symphysis," Sep. 20, 2018, 5 pages.
Swathi Ravi, et al., "Biomaterials for Vascular Tissue Engineering," Nov. 1, 2010, 13 pages.
Boston Scientific, "Spectra Concealable Penile Implant," Sep. 26, 2018, 3 pages.
Wikipedia, "Vascular Bypass," Sep. 18, 2018, 5 pages.
Zephyr Surgical Implants, "Inflatable Penile Implant, ZSI 475," Jun. 20, 2018, 6 pages.
International Searching Authority, "Notification of Transmittal of the International Search Report and the Written Opinion of the International Searching Authority," dated Apr. 9, 2020, in International application No. PCT/US2019/059082.

* cited by examiner

EXPANDABLE PENILE PROSTHESIS

CROSS-REFERENCE TO RELATED APPLICATION

This application claims priority to U.S. Provisional Patent Application No. 62/753,128 filed on Oct. 31, 2018 and entitled "Expandable Penile Prosthesis", the content of which is hereby incorporated by reference.

TECHNICAL FIELD

Embodiments of the invention are in the field of prosthetics.

BACKGROUND

Phalloplasty is the construction or reconstruction of a penis, or the artificial modification of the penis by surgery. Phalloplasty may involve taking a flap of tissue from a donor site to form a phallus. Phalloplasty may further include extending the urethra. Scrotoplasty can be performed using the labia majora (vulva) to form a scrotum where prosthetic testicles can be inserted. Phalloplasty may require an implanted prosthesis to achieve an erection. There are several types of penile prostheses, including malleable rod-like medical devices that allow the neo-penis to either stand up or hang down.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

DETAILED DESCRIPTION

Figure 1:
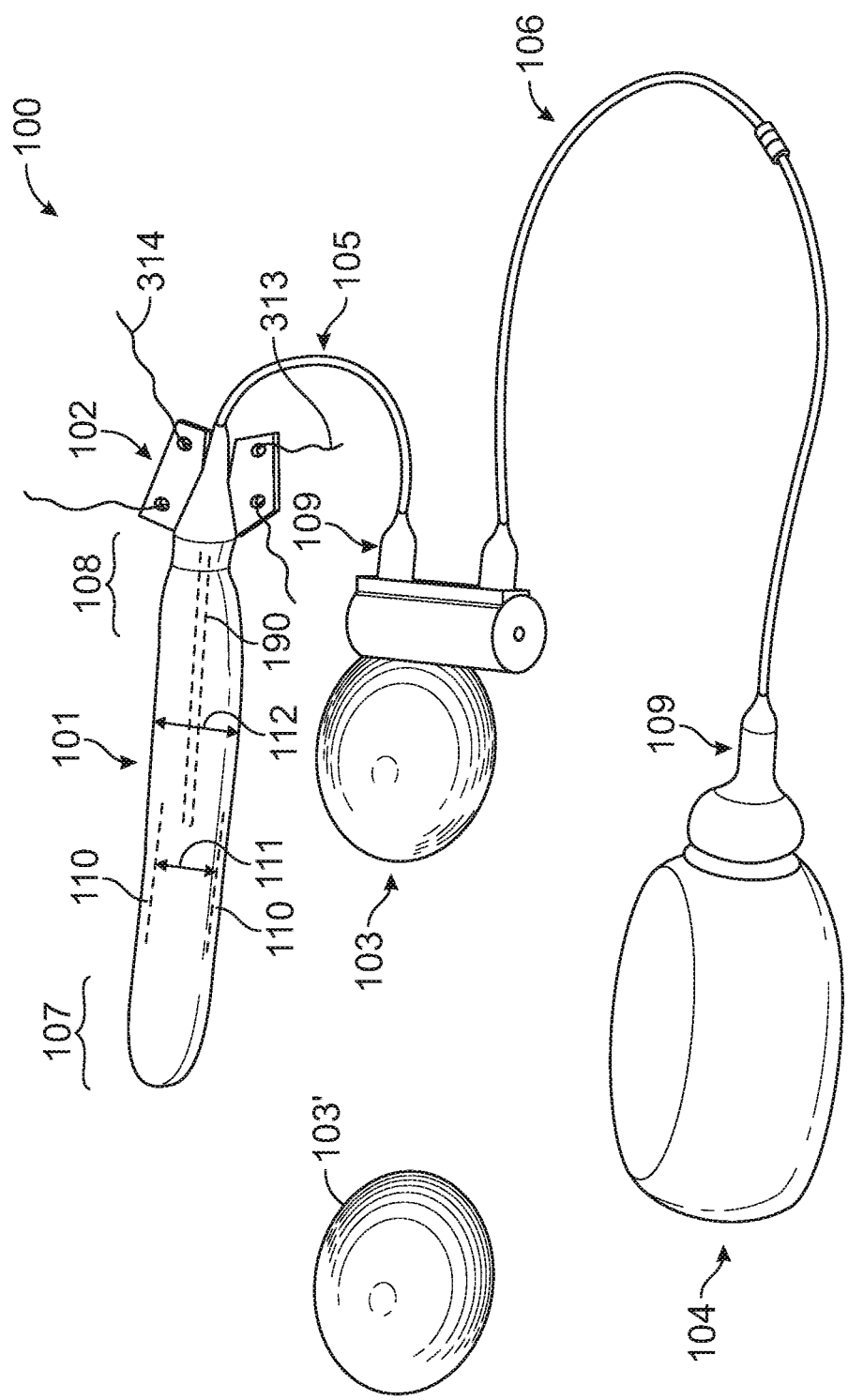
FIG. 1 includes a prosthetic in an embodiment.

Reference will now be made to the drawings wherein like structures may be provided with like suffix reference designations. In order to show the structures of various embodiments more clearly, the drawings included herein are diagrammatic representations of structures. Thus, the actual appearance of the fabricated structures, for example in a photograph, may appear different while still incorporating the claimed structures of the illustrated embodiments. Moreover, the drawings may only show the structures useful to understand the illustrated embodiments. Additional structures known in the art may not have been included to maintain the clarity of the drawings. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact.

Applicant determined a number of problems exist with conventional penile prostheses used in phalloplasty. First, such prostheses are better suited to a normal natal male and are not adapted to the anatomy of the transgender population. Second, such prostheses are prone to infection, sometimes suffering 20% infection rates or more.

In contrast, an embodiment addresses these issues and provides numerous advantages over conventional technologies. Such an embodiment includes a penile implant that is made specifically for use in the transgender population. The prosthesis is implanted within a previously created phallus. The following attributes illustrate how embodiments address one or both of the above-mentioned problems.

First, an embodiment addresses the difficulty of anchoring the device to the pubic bone. Embodiments may include sutures (e.g., FiberWire® suture) already connected to a holster/seat mechanism (where the holster/seat mechanism is configured to be affixed to the pubic bone). The holster/seat mechanism may include a plate, such as a steel plate. Other embodiments may include silicon, plastic, metal (e.g., stainless steel), and combinations thereof. Such embodiments may avoid iron such that the patient may still participate in magnetic resonance imaging (MRI). Such a holster/seat mechanism may be non-linear with a curved surface configured to securely mate a rear portion of device to the curved female pubic bone. Such a holster/seat may include one or more apertures for the above-mentioned sutures to affix to.

Second, an embodiment prevents or at least limits the implant from sliding in and out of the phallus fat layer. Failure to prevent or limit such motion dramatically increases damage to, for example, the glans penis. For example, an embodiment may be coated with a vascular graft type material (e.g., polytetrafluoroethylene, expanded polytetrafluoroethylene (ePTFE), polyethylene terephthalate (Dacron®), or polyurethane) that extends along 80% or more of the expandable conduit. Such a coating prevents sliding of the conduit (e.g., during sexual intercourse) by promoting ingrowth between the neophallus and the implant, thereby reducing the chances for erosion of the neophallus (e.g., due to traumatic contact between the conduit and the glans penis). Further, embodiments may be impregnated and/or coated with antibiotics. For example, the expandable conduit (and other portions of the implant in some embodiments) may be coated with Inhibizone®. For example, the expandable conduit (and other portions of the implant in some embodiments) may be coated with minocycline, Rifampin®, or combinations thereof.

Third, embodiments may include differing numbers of expandable (e.g., inflatable) conduits. As used herein, "expandable" includes a situation where a conduit goes from a collapsed or semi-collapsed state to a rigid state based on the addition of a fluid (e.g., saline or air) into the conduit. A single conduit (e.g., cylinder) embodiment may be used when the phallus is formed from the forearm. However, two conduits may be used for anterolateral thigh (ALT) phalloplasty (or any time a neophallus weight warrants additional support) if the neophallus has a weight that requires more support during an erection. Instead of or in addition to inflatable conduits, malleable members (e.g., rods) may be used in some embodiments. To accommodate the weight of a certain phallus, an inflatable cylinder may have a diameter of 17, 18, 19, 20, 21, 22 mm or more. Thus, depending on the size of the phallus embodiments provide varying means with which to gain an erection.

Fourth, embodiments may include a rounded pump bellow that resembles a testicle (e.g., ovular) to be implanted within a newly formed scrotum.

While the majority of embodiments discussed herein are intended for the transgender population, embodiments may be suitable for a normal natal male.

FIG. 1 illustrates a penile prosthetic 100 comprising an expandable conduit 101. The conduit may expand in response to an increased volume of a gas (e.g., carbon dioxide) or liquid (e.g., saline). The increased volume is due to pump 103 transferring a medium (e.g., liquid) from reservoir 104 to pump 103 and then to conduit 101 via conduits 105, 106. Plate 102 couples the expandable conduit to the patient.

The expandable conduit has first and second opposing ends 108, 107. The first end 108 is immediately adjacent to the plate and the second end 107 includes a rounded tip. The rounded tip provides an advantage over more pointed conventional technologies. A pointed end may cause trauma to the neophallus during strenuous activity (e.g., sexual intercourse).

An embodiment may include an antibiotic on the expandable conduit, the pump, and the reservoir. The embodiment may be impregnated within the materials used to form any of the conduit, pump, and/or reservoir. For example, the antibiotic may be included within silicon used to form conduit 101.

In an embodiment the prosthetic 100 comprises at least one of polytetrafluoroethylene, ePTFE, Dacron®, or polyurethane. For example, such a material may be embedded or otherwise fixedly attached (e.g., a polyurethane mesh or foam attached to a silicon conduit using a fibrin glue) to the conduit 101. Such a material may be woven or otherwise included within fibers, such as a mesh. The material may promote ingrowth of tissue from the neophallus to the conduit 101. As a result, the conduit may slide less within the neophallus during periods of stress (e.g., sexual intercourse). This reduction of movement of conduit 101 with regard to the neophallus may limit irritation to the tissue of the neophallus and possibly avoid infection of the neophallus, thinning of the walls of the neophallus, and/or general trauma to the neophallus that may lead to rejection or failure of system 100.

In an embodiment the prosthetic 100 comprises a protein. For example, the protein may include at least one of collagen or fibrin and may be on conduit 101. Such a protein may promote ingrowth of tissue from the neophallus to the conduit 101. As a result, the conduit may slide less within the neophallus during periods of stress (e.g., sexual intercourse). This reduction of movement of conduit 101 with regard to the neophallus may limit irritation to the tissue of the neophallus and possibly avoid infection of the neophallus, thinning of the walls of the neophallus, and/or general trauma to the neophallus that may lead to rejection or failure of system 100.

In an embodiment the prosthetic 100 comprises at least one of polyglycolic acid, polyhydroxyalkanoate, polycaprolactone, or polyethylene glycol (e.g., on conduit 101). Such a material may promote ingrowth of tissue from the neophallus to the conduit 101 as described above.

In an embodiment the prosthetic 100 comprises at least one of a foam or a hydrogel (e.g., a polyurethane foam on conduit 101). Such a material may promote ingrowth of tissue from the neophallus to the conduit 101 as described above.

In an embodiment system 100 includes an additional expandable conduit, wherein the additional expandable conduit is coupled to the pump 103 via at least one of conduit 105 or another conduit (not shown in FIG. 1). For instance, an embodiment may include coupler 109 to couple conduit 105 to pump 103. However, another coupler similar to coupler 109 may be sealed. If the physician desires to use an additional conduit (similar to conduit 101), the physician may separate the seal of the additional coupler from the additional coupler to allow for a fluid connection between the additional conduit and the pump. In such a case the physician may choose a larger volume reservoir 104 to provide added volume of saline for the additional conduit.

A kit may include numerous reservoirs of varying size along with one or more conduits 101 and pump 103. The kit may include a resilient ellipse 103'. Such an ellipse may be used as a separate testicle within a newly formed scrotum. Thus, pump 103 and ellipse 103' may collectively provide the patient with two artificial testicles. As used herein, a circle is a special form of ellipse where the two foci of the ellipse are at the same location.

Embodiments of implants for transgender phalloplasty differ in their tasks from the tasks faced by prosthetics for natal males, such as prosthetics used to treat erectile dysfunction (ED). For example, the composition of the neophallus includes fatty tissue and may be significantly heavier than an average natal penis. As a result, the neophallus may be heavier than a typical penis. Further, an implant for a natal male may not need a plate, such as plate 102, because the natal male may anchor an expandable conduit to the corpora cavernosa, which is nonexistent in the natale female anatomy.

Thus, embodiments address these issues in various ways, including plate 102 as well as other ways. For example, in an embodiment the conduit 101 has a side wall 110 that surrounds a void 111 (where void 111 fills with fluid from pump 103). To accommodate the relative increased weight of a neophallus, the side wall includes a thickness of between 0.1 and 0.5 mm. However, in other embodiments the thickness is between 0.2 and 0.6 or 0.3 and 0.7 mm. Further, in an embodiment conduit 101 includes a maximum diameter 112 of between 15 and 20 mm. However, in other embodiments the diameter is between 17 and 30 mm or between 20 and 30 mm.

An embodiment may include a malleable member 190 (see FIG. 1) included within the expandable conduit. In an embodiment the member is no greater than 75% of the length of conduit 101. As such, the malleable member may provide some support for an erection while further support is offered by expansion of the conduit 101.

An embodiment includes pump 103, which may be configured to prevent unintended inflation of conduit 101. For example, a patient may wish to avoid an unintended erection brought on by an advertent manipulation of system 100 (e.g., inadvertent compression of a pump when a patient is crouching over to tie one's shoelaces). Thus, an embodiment includes a pump such as a pump described in U.S. Pat. No. 7,637,861 (which issued Dec. 29, 2009 and is assigned to Boston Scientific Scimed, Inc.). U.S. Pat. No. 7,637,861 is hereby incorporated by reference. However, other embodiments are not limited in this regard and may use other forms of pumps that may or may not be adapted to avoid an unintended erection.

Figure 2A:
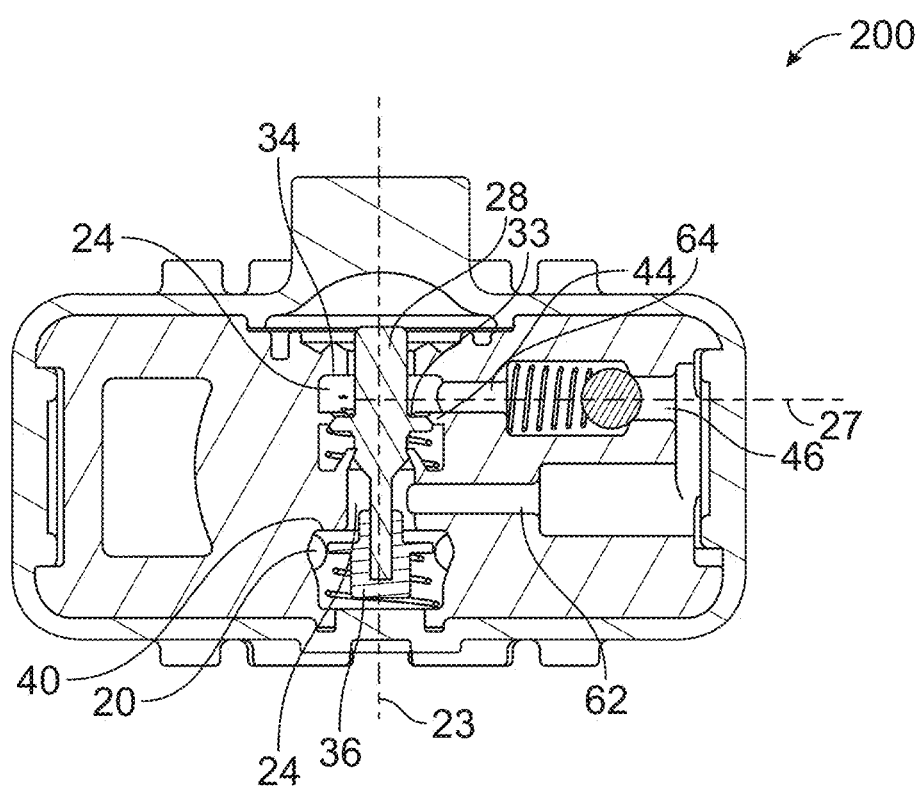
FIGS. 2A and 2B include a pump in an embodiment.
Figure 2B:
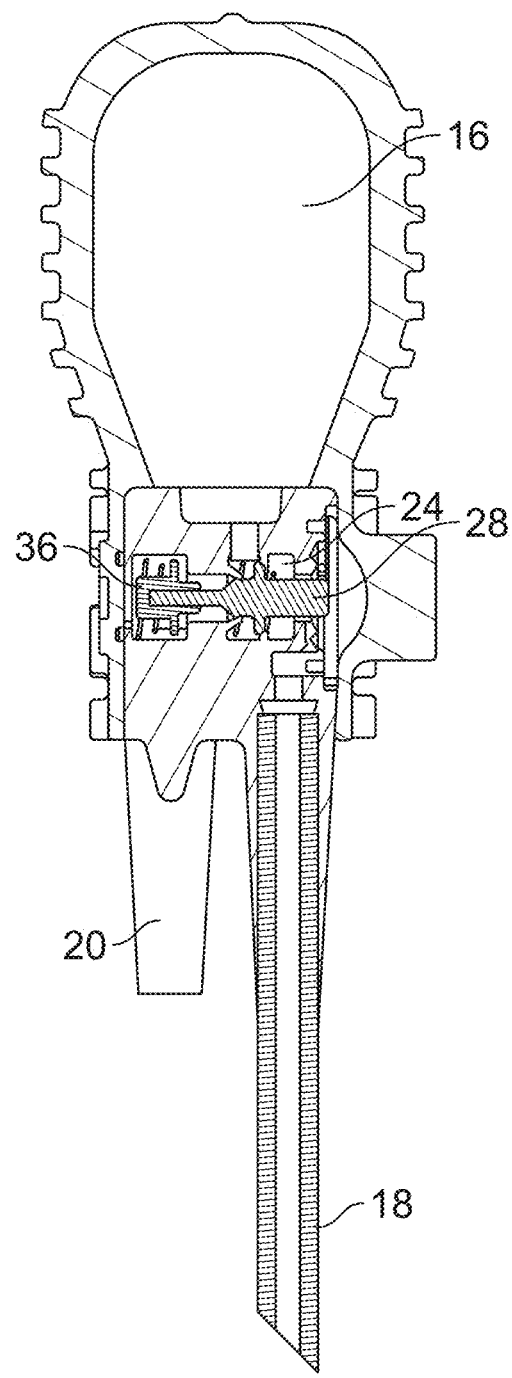

FIGS. 2A and 2B include an embodiment of a pump 200. Pump 200 comprises a pump housing having a fluid passageway 24, first and second fluid ports 18, 20 in fluid communication with the fluid passageway and operatively connectable to a fluid reservoir (e.g., reservoir 104 via port 18) and an expandable conduit (e.g., conduit 101 via port 20). Pump 200 includes a pump bulb 16 in fluid communication with the fluid passageway 24 that can be operated to transfer fluid between the first and second fluid ports through the fluid passageway. Pump 200 includes a poppet 28 positioned within the fluid passageway, the poppet having an extending portion extending away from a body portion of the poppet, the extending portion having a sealing surface 33 biased toward a valve seat 34 within the fluid passageway. A flange 44 extends from a surface of the fluid passageway and toward the interior of the fluid passageway and is spaced from the valve seat within the fluid passageway. A fluid path 62, 64 is between the extending portion of the poppet and the flange when the extending portion of the poppet is in contact with the flange wherein the fluid path can allow fluid to pass from one side of the flange to the other. Pump 200 comprises another poppet 36. The poppets 28, 36 are positioned within the fluid passageway aligned along a valve axis 23 and biased toward valve seats 34, 40 within the fluid passageway. Poppet 28 comprises an end slidingly engaged with an end of poppet 36. A bypass chamber 46 is fluidly connected by a bypass input channel 62 to the fluid passageway at a first location and fluidly connected by a bypass output channel 64 to the fluid passageway at a second location, the bypass chamber comprising a bypass check valve biased toward a closed position along a check valve axis 27.

Figure 3:
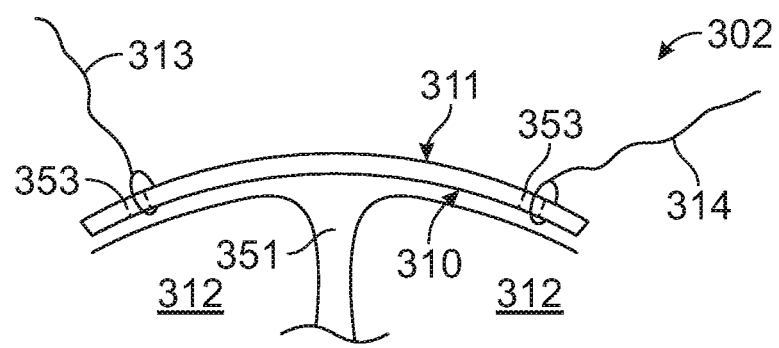
FIG. 3 includes a plate in an embodiment.

FIG. 3 discloses an embodiment of a plate 302. Plate 302 includes a concave surface 310. When implanted surface 310 is between surface 311 and pubic bone 312. In an embodiment surface 311 is convex but in other embodiments may be planar. In an embodiment at least one suture 313, 314 is coupled to the plate. The concave surface 310 better conforms to the arch of pubic bone 312 and extends across pubic symphysis 351 such that apertures 353 are aligned over bone 312.

Figure 4:
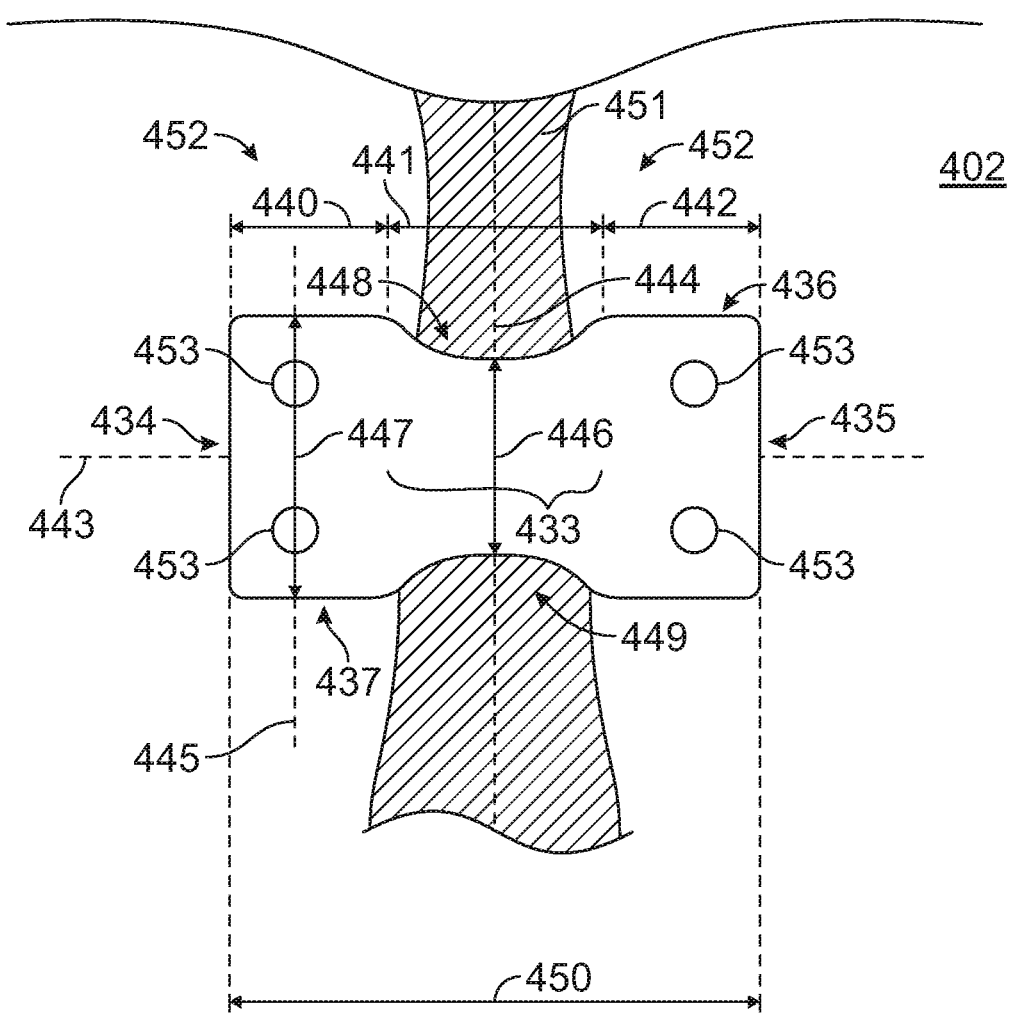
FIG. 4 includes a plate in an embodiment.

FIG. 4 discloses an embodiment of a plate 402. Plate 402 includes a malleable portion 433. This is not to say portions outside portion 433 are not also malleable, only that portion 433 is malleable. In an embodiment the plate 402 includes first and second ends 434, 435 that oppose each other. The malleable portion 433 is included between ends 434, 435 and in a middle third 441 of the plate. The middle portion 441 of the plate is between a first outer third of the plate 440 and a second outer third of the plate 442. In an embodiment the first outer third of the plate 440 is less malleable than the malleable portion of the plate 433.

In an embodiment a first axis 443 intersects the first and second ends 434, 435. The plate includes third and fourth ends 436, 437 that oppose each other. A second axis 444 intersects the third and fourth ends 436, 437. The first axis 443 is orthogonal to the second axis 444. The second axis 444 intersects the middle third of the plate 441. A third axis 445 intersects the third and fourth ends and first outer third of the plate 440. The second axis is parallel to the third axis. The third and fourth ends are separated from each other by a first distance 446 measured along the second axis; the third and fourth ends are separated from each other by a second distance 447 measured along the third axis; and the second distance is greater than the first distance. For instance, the depressions 448, 449 may promote malleability for the plate. Further, the plate may include titanium to promote malleability.

In an embodiment, the first end 434 is configured to rotate with respect to the second end 435. This rotation may occur about axis 444. The rotation may be due to malleability of area 433. However, in other embodiments a hinge may be located along axis 444. Use of a hinge may be used with plate having a concave surface 310 or a planar surface (e.g., where surfaces 310, 311 are planar and alignment to curved pubic bone is addressed by the hinge).

In an embodiment the plate has a maximum width 450 of at least 3 cm. However, in other embodiments, width 450 may be 4, 5, 6 cm or more. This helps ensure the plate can span the pubic symphysis 451 (which may be 1 cm in breadth) so bone anchoring elements can attach to pubic bone 452. For example, sutures or bone screws may couple the plate to bone 452 at apertures 453.

Figure 5:
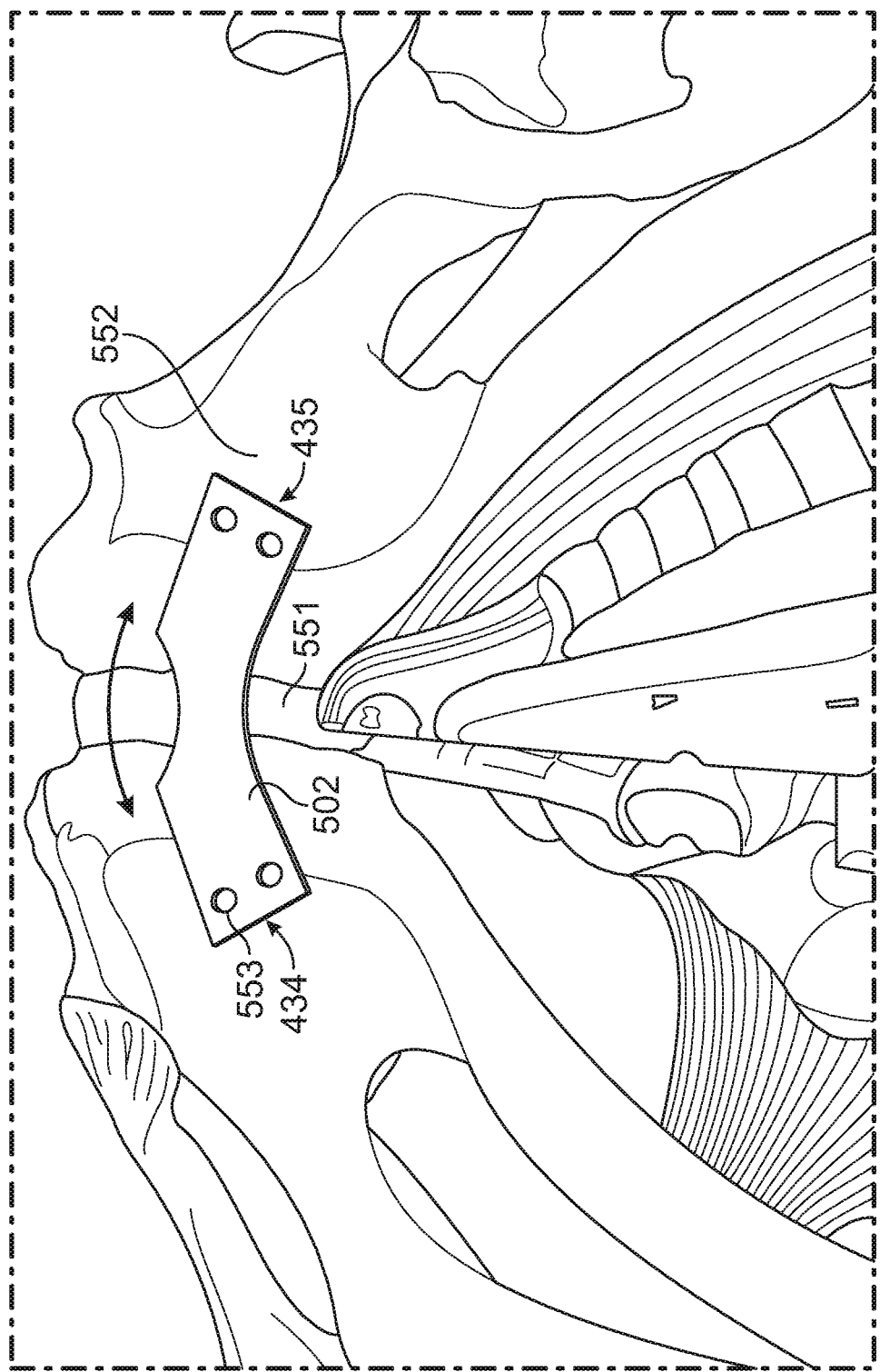
FIG. 5 includes a plate in an embodiment.
Figure 6:
FIG. 6 includes a plate in an embodiment.
Figure 7:
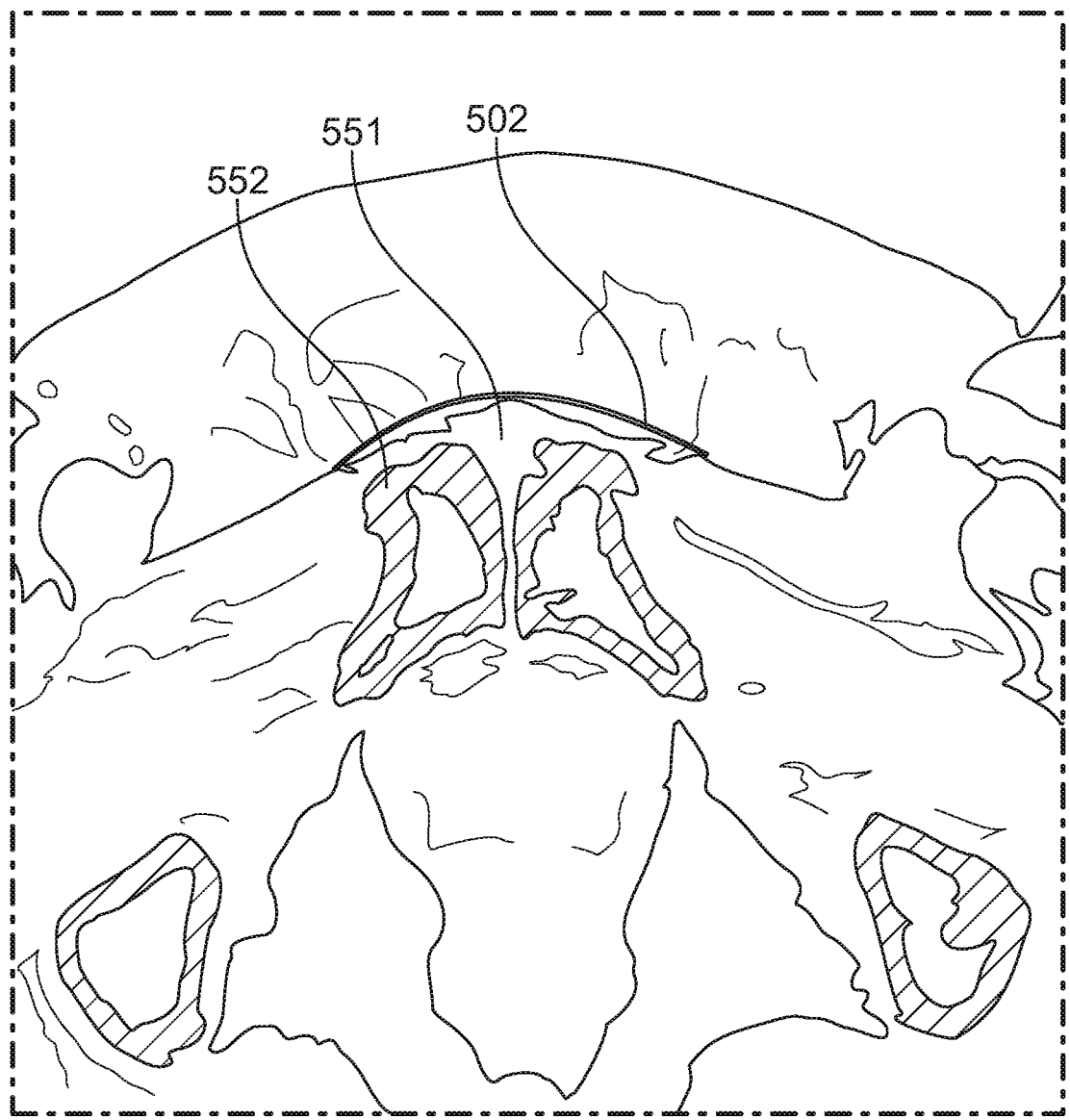
FIG. 7 includes a plate in an embodiment.

FIGS. 5, 6, 7 illustrate how a plate 502 can span the pubic symphysis 551 so bone screws or sutures can couple the plate to bone 552 (e.g., via apertures 553). Further, the ability to rotate the ends 434, 435 about a middle portion of the plate helps accommodate the varied anatomy illustrated in FIGS. 6 and 7. By affixing to bone instead of the pubic symphysis 551 a more stable implant is obtained such that the implant can better tolerate long term forces such as those sustained during sexual intercourse over many years. By providing an ability to rotate about region 441, a better fit and more stable to the arched bone is achieved.

Figure 8:
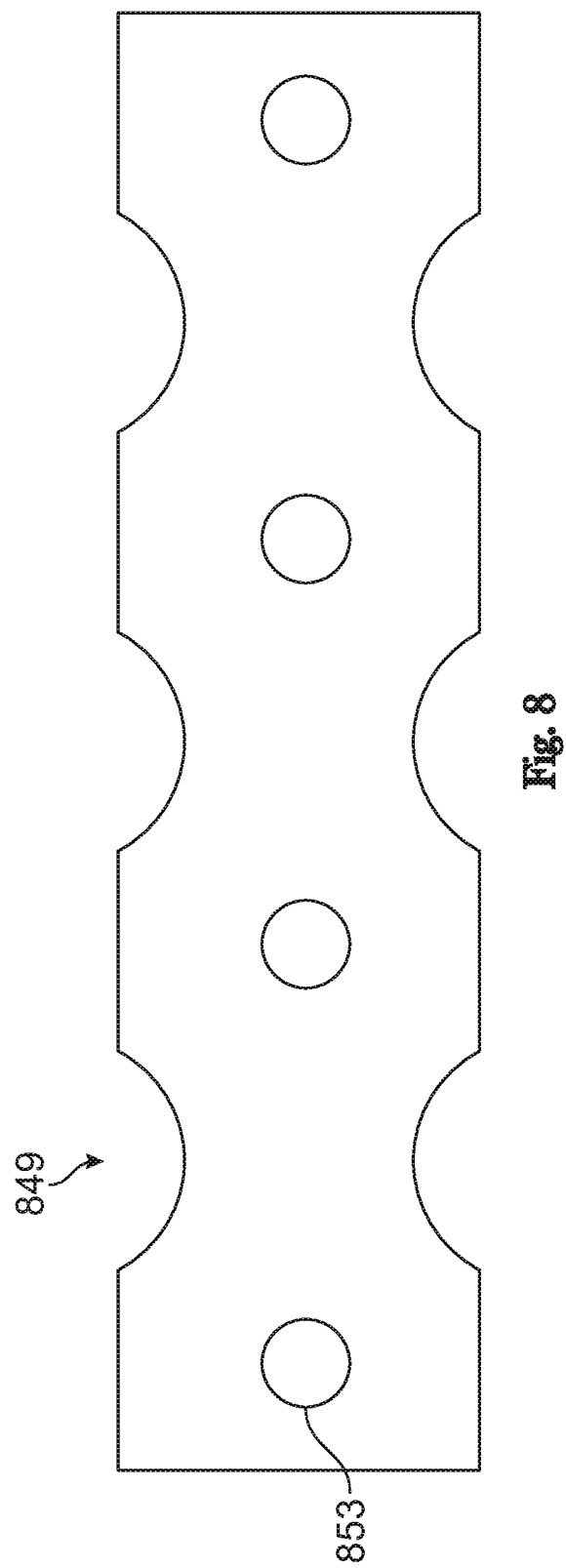
FIG. 8 includes a plate in an embodiment.

FIG. 8 includes an embodiment with additional apertures 853 for bone screws/suture and additional depressions 849 that promote malleability.

The plate may include at least one of titanium, cobalt, or chromium. This may promote compatibility with MRI technologies. Further, plates may include stainless steel with a low enough iron grade to promote compatibility with MRI technologies.

An embodiment may include a penile prosthetic comprising: a conduit; a malleable material included within the conduit; a plate that couples to the conduit, wherein the plate includes a concave surface. Thus, not all embodiments necessarily require an inflatable conduit and pump. Some embodiments may provide a semi-rigid embodiment where the user manually adjusts the malleable component (e.g., a malleable rod) to achieve an erection and then manually lowers the prosthetic when an erection is no longer desired. The conduit may include silicon that surrounds a malleable MRI compatible rod (e.g. a rod made from titanium).

As used herein, a conduit includes a channel through which something (such as a fluid) is conveyed. For example, a urethra may pass through the conduit. The conduit may be otherwise solid with the exception of the urethra (natural or artificial). As used herein, a "rod" may be solid or in include voids within the rod.

The following examples pertain to further embodiments.

Example 1

A penile prosthetic comprising: an expandable conduit; a pump; a reservoir; a first conduit that couples the expandable conduit to the pump; a second conduit that couples the reservoir to the pump; and a plate that couples to the expandable conduit, wherein the plate includes a concave surface.

Example 2

The prosthetic of example 1, wherein: the plate includes a flat surface; the flat surface is opposite the concave surface.

Example 3

The prosthetic of example 1, wherein: the expandable conduit has first and second opposing ends; the first end is immediately adjacent to the plate; the second end includes a rounded tip.

Example 4

The prosthetic of example 3 comprising an antibiotic on the expandable conduit, the pump, and the reservoir.

Example 5

The prosthetic of example 4 comprising at least one suture coupled to the plate.

Example 6

The prosthetic of example 4 comprising at least one of polytetrafluoroethylene, expanded polytetrafluoroethylene (ePTFE), polyethylene terephthalate (Dacron®), or polyurethane.

Such materials may be formed as a layer over the conduit and may provide a scaffold for tissue ingrowth, which may help stabilize the conduit during strenuous activity. This stability may avoid trauma to tissue of the neophallus and thereby avoid tissue irritation and complications. Such a layer may be combined with, for example, an antibiotic.

Example 7

The prosthetic of example 6 comprising a protein.

Example 8

The prosthetic of example 7 wherein the protein includes at least one of collagen or fibrin.

Example 9

The prosthetic of example 4 comprising a protein.

Example 10

The prosthetic of example 9 wherein the protein includes at least one of collagen or fibrin.

Example 11

The prosthetic of example 4 comprising at least one of a foam or a hydrogel.

Example 12

The prosthetic of example 4 comprising at least one of polyglycolic acid, polyhydroxyalkanoate, polycaprolactone, or polyethylene glycol.

Example 13

The prosthetic of example 4 comprising an additional expandable conduit, wherein the additional expandable conduit is coupled to the pump via at least one of the first conduit or a third conduit.

For example, a single conduit may suffice for a neophallus formed from a forearm but two or more conduits may be needed for a larger neophallus formed from a thigh.

Example 14

The prosthetic of example 4 wherein: the first conduit has a side wall; the side wall includes a thickness of between 0.1 and 0.5 mm.

Such a thickness may be critical in some embodiments. For instance, a neophallus formed from a thigh may be of such weight that a more rigid and mechanically sound conduit may be needed to support the neophallus when the conduit is inflated to an expanded state. Applicant determined the thickness of between 0.1 and 0.5 mm provides ample support for such a neophallus. This is in contrast to conventional prosthetics used for natal males.

Example 15

The prosthetic of example 14 wherein the first conduit includes a maximum diameter of between 15 and 20 mm.

Such a diameter may be critical in some embodiments. For instance, a neophallus formed from a thigh may be of such weight that a more rigid and mechanically sound conduit may be needed to support the neophallus when the conduit is inflated to an expanded state. Applicant determined the diameter of between 15 and 20 mm provides ample support for such a neophallus. This is contrast to conventional prosthetics used for natal males.

Example 16

The prosthetic of example 15 wherein the pump comprises: a pump housing having a fluid passageway; first and second fluid ports in fluid communication with the fluid passageway and operatively connectable to a fluid reservoir and at the expandable conduit, respectively; a pump bulb in fluid communication with the fluid passageway that can be operated to transfer fluid between the first and second fluid ports through the fluid passageway; a first poppet positioned within the fluid passageway, the first poppet having an extending portion extending away from a body portion of the first poppet, the extending portion having a sealing surface biased toward a valve seat within the fluid passageway; a flange extending from a surface of the fluid passageway and toward the interior of the fluid passageway and spaced from the valve seat within the fluid passageway; and a fluid path between the extending portion of the first poppet and the flange when the extending portion of first poppet is in contact with the flange wherein the fluid path can allow fluid to pass from one side of the flange to the other.

Example 17

The prosthetic of example 16, wherein: the pump comprises a second poppet; the first and second poppets are positioned within the fluid passageway and are aligned along a valve axis and biased toward first and second valve seats within the fluid passageway, respectively.

Example 18

The prosthetic of example 16, wherein the first poppet comprises an end slidingly engaged with an end of the second poppet.

Example 19

The prosthetic of example 18 comprising a bypass chamber fluidly connected by a bypass input channel to the fluid passageway at a first location and fluidly connected by a bypass output channel to the fluid passageway at a second location, the bypass chamber comprising a bypass check valve biased toward a closed position along a check valve axis.

Example 20

The prosthetic of example 19, wherein the check valve axis is oriented in a non-parallel manner with respect to the valve axis of the first and second poppets.

Example 21

The prosthetic of example 15 wherein the pump comprises: a pump housing having a fluid passageway; first and second fluid ports in fluid communication with the fluid passageway and operatively connectable to a fluid reservoir and the expandable conduit, respectively; a pump bulb in fluid communication with the fluid passageway that can be operated to transfer fluid between the first and second fluid ports through the fluid passageway; and first and second poppets positioned within the fluid passageway and biased toward first and second valve seats within the fluid passageway, respectively, the first poppet having an end slidingly engaged with an end of the second poppet.

Example 22

The prosthetic of example 16 comprising a resilient ellipse, wherein: the pump is resilient and includes an elliptical surface; the pump is not monolithic with the resilient ellipse.

For example, the pump and resilient ellipse may be two separate pieces.

Example 23

The prosthetic of example 1 wherein the plate includes a malleable portion.

As used herein, "malleable" means capable of being shaped by a medical provider without use of a hammer, rollers, special tools, or the like. A medical provider of average strength (e.g., a 40-year-old male) may use his or her hands (possibly with forceps, pliers, and the like) to shape a "malleable" plate to better fit an anatomical structure.

Example 24

The prosthetic of example 23 wherein: the plate includes first and second ends that oppose each other; the malleable portion is included in a middle third of the plate; the middle portion of the plate is between a first outer third of the plate and a second outer third of the plate.

Example 25

The prosthetic of example 24 wherein the first outer third of the plate is less malleable than the malleable portion of the plate.

Example 26

The prosthetic of example 25 wherein: a first axis intersects the first and second ends; the plate includes third and fourth ends that oppose each other; a second axis intersects the third and fourth ends; the first axis is orthogonal to the second axis; the second axis intersects the middle third of the plate; a third axis intersects the third and fourth ends and first outer third of the plate; the second axis is parallel to the third axis; the third and fourth ends are separated from each other by a first distance measured along the second axis; the third and fourth ends are separated from each other by a second distance measured along the third axis; the second distance is greater than the first distance.

Example 27

The prosthetic of example 16 wherein: the plate includes first and second opposing ends; the first end is configured to rotate with respect to the second end.

Example 28

The prosthetic of example 27 wherein the plate has a maximum width of at least 3 cm.

Such a maximum width may be critical in some embodiments. For instance, a neophallus formed from a thigh may be of such weight that a more rigid and mechanically sound base (to mount the conduit) may be needed to support the neophallus when the conduit is inflated to an expanded state. Applicant determined the maximum width of at least 3 cm provides a plate that is stable enough to support such a neophallus.

Example 29

The prosthetic of example 28 wherein the plate includes at least one of titanium, cobalt, or chromium.

Example 30

The prosthetic of example 29 wherein: the plate includes first and second apertures; the first aperture is adjacent the first end of the plate and the second aperture is adjacent the second end of the plate; the first and second apertures are at least 3 cm from one another.

Applicant determined this width would promote stability of the plate with regard to the patient's bone tissue.

Example 31

The prosthetic of example 30 comprising at least one suture coupled to the first and second apertures.

Example 32

The prosthetic of example 30 comprising a malleable member included within the expandable conduit.

Example 33

The prosthetic of example 32 wherein: the expandable conduit has a first length; the malleable member has a second length; the second length is no greater than 75% of the first length.

Example 34

A penile prosthetic comprising: an expandable conduit; a pump; a reservoir; a first conduit that couples the expandable conduit to the pump; a second conduit that couples the reservoir to the pump; and a plate that couples to the expandable conduit, wherein the plate includes a concave surface.

Example 35

The prosthetic of example 34, wherein: the expandable conduit has first and second opposing ends; the first end is immediately adjacent to the plate; the second end includes a rounded tip.

Example 36

The prosthetic of example 35 comprising an antibiotic on the expandable conduit, the pump, and the reservoir.

Example 37

The prosthetic of example 36 comprising at least one of polytetrafluoroethylene, expanded polytetrafluoroethylene (ePTFE), polyethylene terephthalate (Dacron®), or polyurethane.

Example 38

The prosthetic of example 37 wherein: the first conduit has a side wall; the side wall includes a thickness of between 0.1 and 0.5 mm.

Example 39

The prosthetic of example 38 wherein the first conduit includes a maximum diameter of between 15 and 20 mm.

Example 40

The prosthetic of example 39 wherein the pump comprises: a pump housing having a fluid passageway; first and second fluid ports in fluid communication with the fluid passageway and operatively connectable to a fluid reservoir and at the expandable conduit, respectively; a pump bulb in fluid communication with the fluid passageway that can be operated to transfer fluid between the first and second fluid ports through the fluid passageway; a first poppet positioned within the fluid passageway, the first poppet having an extending portion extending away from a body portion of the first poppet, the extending portion having a sealing surface biased toward a valve seat within the fluid passageway; a flange extending from a surface of the fluid passageway and toward the interior of the fluid passageway and spaced from the valve seat within the fluid passageway; and a fluid path between the extending portion of the first poppet and the flange when the extending portion of first poppet is in contact with the flange wherein the fluid path can allow fluid to pass from one side of the flange to the other.

Example 41

The prosthetic of example 40, wherein: the pump comprises a second poppet; the first and second poppets are positioned within the fluid passageway and are aligned along a valve axis and biased toward first and second valve seats within the fluid passageway, respectively.

Example 42

The prosthetic of example 41, wherein the first poppet comprises an end slidingly engaged with an end of the second poppet.

Example 43

The prosthetic of example 42 comprising a bypass chamber fluidly connected by a bypass input channel to the fluid passageway at a first location and fluidly connected by a bypass output channel to the fluid passageway at a second location, the bypass chamber comprising a bypass check valve biased toward a closed position along a check valve axis.

Example 43

The prosthetic of example 39 wherein the pump comprises: a pump housing having a fluid passageway; first and second fluid ports in fluid communication with the fluid passageway and operatively connectable to a fluid reservoir and the expandable conduit, respectively; a pump bulb in fluid communication with the fluid passageway that can be operated to transfer fluid between the first and second fluid ports through the fluid passageway; and first and second poppets positioned within the fluid passageway and biased toward first and second valve seats within the fluid passageway, respectively, the first poppet having an end slidingly engaged with an end of the second poppet.

Example 44

The prosthetic of example 43 wherein: the plate includes first and second ends that oppose each other; the malleable portion is included between in a middle third of the plate; the middle portion of the plate is between a first outer third of the plate and a second outer third of the plate.

Example 45

The prosthetic of example 44 wherein: a first axis intersects the first and second ends; the plate includes third and fourth ends that oppose each other; a second axis intersects the third and fourth ends; the first axis is orthogonal to the second axis; the second axis intersects the middle third of the plate; a third axis intersects the third and fourth ends and first outer third of the plate; the second axis is parallel to the third axis; the third and fourth ends are separated from each other by a first distance measured along the second axis; the third and fourth ends are separated from each other by a second distance measured along the third axis; the second distance is greater than the first distance.

Example 46

The prosthetic of example 43 wherein: the plate includes first and second opposing ends; the first end is configured to rotate with respect to the second end.

Example 47

The prosthetic of example 46 wherein the plate has a maximum width of at least 3 cm.

Example 48

The prosthetic of example 47 wherein the plate includes at least one of titanium, cobalt, or chromium.

Example 49

The prosthetic of example 48 wherein: the plate includes first and second apertures; the first aperture is adjacent the first end of the plate and the second aperture is adjacent the second end of the plate; the first and second apertures are at least 3 cm from one another.

Example 50

The prosthetic of example 49 comprising at least one suture coupled to the first and second apertures.

Example 51

A penile prosthetic comprising: a conduit; a malleable material included within the conduit; a plate that couples to the conduit, wherein the plate includes a concave surface.

Example 52

The prosthetic of example 51 comprising a rod that includes the malleable material.

Example 53

The prosthetic of example 52 comprising a pliable material, wherein: the conduit has a long axis and short axis; the rod is oriented substantially parallel to the long axis; the pliable material surrounds the rod in a plane, the plane being orthogonal to the long axis.

Example 52

The prosthetic of example 53 comprising a terminal cap wherein: the terminal cap includes an aperture having a first diameter; the conduit has a second diameter; the first diameter is between 0% and 5% greater than the second diameter such that the terminal cap is configured to couple to an end of the conduit; the terminal cap includes the pliable material but not the malleable material.

Example 53

The prosthetic of example 51 comprising at least one suture coupled to the plate.

Example 54

The prosthetic of example 51 comprising at least one of polytetrafluoroethylene, expanded polytetrafluoroethylene (ePTFE), polyethylene terephthalate (Dacron®), or polyurethane.

Example 55

The prosthetic of example 51 wherein the conduit includes a maximum diameter of between 15 and 20 mm.

Example 56

The prosthetic of example 51 wherein the plate includes a malleable portion.

Example 57

The prosthetic of example 56 wherein: the plate includes first and second ends that oppose each other; the malleable portion is included in a middle third of the plate; the middle portion of the plate is between a first outer third of the plate and a second outer third of the plate.

Example 58

The prosthetic of example 57 wherein the first outer third of the plate is less malleable than the malleable portion of the plate.

Example 59

The prosthetic of example 57 wherein: a first axis intersects the first and second ends; the plate includes third and fourth ends that oppose each other; a second axis intersects the third and fourth ends; the first axis is orthogonal to the second axis; the second axis intersects the middle third of the plate; a third axis intersects the third and fourth ends and first outer third of the plate; the second axis is parallel to the third axis; the third and fourth ends are separated from each other by a first distance measured along the second axis; the third and fourth ends are separated from each other by a second distance measured along the third axis; the second distance is greater than the first distance.

Example 60

The prosthetic of example 56 wherein: the plate includes first and second opposing ends; the first end is configured to rotate with respect to the second end.

Example 61

The prosthetic of example 56 wherein the plate has a maximum width of at least 3 cm.

Example 62

The prosthetic of example 61 wherein the plate includes at least one of titanium, cobalt, or chromium.

Example 63

The prosthetic of example 62 wherein: the plate includes first and second apertures; the first aperture is adjacent a first end of the plate and the second aperture is adjacent a second end of the plate, the second end being opposite the first end; the first and second apertures are at least 3 cm from one another.

Example 64

The prosthetic of example 63 comprising at least one suture coupled to the first and second apertures.

Example 65

The prosthetic of example 63 comprising a rod that includes the malleable material, wherein: the conduit has a first length; the rod has a second length; the second length is no greater than 75% of the first length.

Example 1a

A penile prosthetic comprising: an expandable conduit; a pump; a reservoir; a first conduit that couples the expandable conduit to the pump; a second conduit that couples the reservoir to the pump; and a plate that couples to the expandable conduit, wherein the plate includes a concave surface; wherein: (a)(i) the expandable conduit has first and second opposing conduit ends; (a)(ii) the first conduit end is immediately adjacent to the plate; (a)(iii) the second conduit end includes a rounded tip; wherein: (b)(i) the first conduit has a side wall; (b)(ii) the side wall includes a thickness of between 0.1 and 0.5 mm; wherein the first conduit includes a maximum diameter of between 15 and 20 mm; wherein (c)(i) the plate includes a malleable portion; (c)(ii) the plate includes first and second opposing plate ends; (c)(iii) the first plate end is configured to rotate with respect to the second plate end; wherein: (d)(i) the plate includes first and second apertures; (d)(ii) the first aperture is adjacent the first plate end and the second aperture is adjacent the second plate end; (d)(iii) the first and second apertures are at least 3 cm from one another; (d)(iv) the plate has a maximum width of at least 3 cm.

For example, the reservoir may be external of the pump as shown in FIG. 1. However, the reservoir may be included within a pump housing in other embodiments. The first and second conduits may be external to a pump housing as shown in FIG. 1 or internal to a housing, such as a pump housing, in other embodiments. The conduits may be relatively long as shown in FIG. 1 or rather short, such as short passages or openings in other embodiments.

By "immediately adjacent" such as "first conduit end is immediately adjacent to the plate", the first conduit may be within 2 to 4 cm of the plate in some embodiments or between 3 to 5 cm or 4 to 6 cm in other embodiments. An aperture may be "adjacent" a plate end by being within 1 to 2 cm of an end or side of the plate. However, in other embodiments the aperture may be adjacent a plate end by being within 3 to 4 cm or 4 to 5 cm of an end or side of the plate.

An aperture does not necessarily require an enclosed hole. An aperture may include an opening, hole, or gap. The aperture may be configured to accept a suture, screw, or anchor.

The "malleable" portion may be limited to a certain subset area of the plate or may include the entire plate. By "rotate" the ends of the plates may bend about a location with respect to each other.

Another Version of Example 1a

A penile prosthetic comprising: an expandable conduit; a pump; a reservoir that is coupled the expandable conduit and the pump; and a plate that couples to the expandable conduit, wherein the plate includes a concave surface; wherein: (a)(i) the expandable conduit has first and second opposing conduit ends; (a)(ii) the first conduit end is immediately adjacent to the plate; (a)(iii) the second conduit end includes a rounded tip; wherein: (b)(i) the first conduit has a side wall; (b)(ii) the side wall includes a thickness of between 0.1 and 0.5 mm; wherein the first conduit includes a maximum diameter of between 15 and 20 mm; wherein (c)(i) the plate includes a malleable portion; (c)(ii) the plate includes first and second opposing plate ends; (c)(iii) the first plate end is configured to rotate with respect to the second plate end; wherein: (d)(i) the plate includes first and second apertures; (d)(ii) the first aperture is adjacent the first plate end and the second aperture is adjacent the second plate end; (d)(iii) the first and second apertures are at least 3 cm from one another; (d)(iv) the plate has a maximum width of at least 3 cm.

For instance, some embodiments may forego the first and second conduits of other examples addressed herein.

Another Version of Example 1a

A penile prosthetic comprising: an expandable conduit; a pump; a reservoir; a first conduit that couples the expandable conduit to the pump; a second conduit that couples the reservoir to the pump; and a plate that couples to the expandable conduit, wherein the plate includes a concave surface; wherein: (a)(i) the expandable conduit has first and second opposing conduit ends; (a)(ii) the first conduit end is immediately adjacent to the plate; (a)(iii) the second conduit end includes a rounded tip; wherein (b)(i) the plate includes a malleable portion; (b)(ii) the plate includes first and second opposing plate ends; (b)(iii) the first plate end is configured to rotate with respect to the second plate end; wherein: (b)(i) the plate includes first and second apertures; (b)(ii) the first aperture is adjacent the first plate end and the second aperture is adjacent the second plate end.

Another Version of Example 1a

A penile prosthetic comprising: an expandable conduit; a pump; a reservoir; a first conduit that couples the expandable conduit to the pump; a second conduit that couples the reservoir to the pump; and a plate that couples to the expandable conduit, wherein the plate includes a concave surface; wherein: (a)(i) the expandable conduit has first and second opposing conduit ends; (a)(ii) the first conduit end is immediately adjacent to the plate; (a)(iii) the second conduit end includes a rounded tip; wherein: (b)(i) the first conduit has a side wall; (b)(ii) the side wall includes a thickness of between 0.1 and 0.5 mm; wherein the first conduit includes a maximum diameter of between 15 and 20 mm; wherein (c)(i) the plate includes a malleable portion; (c)(ii) the plate includes first and second opposing plate ends; (c)(iii) the first plate end is configured to rotate with respect to the second plate end; wherein: (d)(i) the plate includes first and second apertures; (d)(ii) the first aperture is adjacent the first plate end and the second aperture is adjacent the second plate end; (d)(iii) the first and second apertures are at least 3 cm from one another; (d)(iv) the plate has a maximum width of at least 3 cm.

Another Version of Example 1a

A penile prosthetic comprising: an expandable conduit; a pump; a reservoir; a first conduit that couples the expandable conduit to the pump; a second conduit that couples the reservoir to the pump; and a plate that couples to the expandable conduit, wherein the plate includes a concave surface; wherein: (a)(i) the expandable conduit has first and second opposing conduit ends; (a)(ii) the first conduit end is immediately adjacent to the plate; (a)(iii) the second conduit end includes a rounded tip; wherein: (b)(i) the first conduit has a side wall; (b)(ii) the side wall includes a thickness of between 0.1 and 0.5 mm; wherein the first conduit includes a maximum diameter of between 15 and 20 mm; wherein (c)(i) the plate includes a malleable portion; (c)(ii) the plate includes first and second opposing plate ends; (c)(iii) the first plate end is configured to rotate with respect to the second plate end; wherein: (d)(i) the plate includes an aperture; and (d)(ii) the plate has a maximum width of at least 3 cm.

For instance, the plate may include a single aperture that is receptive to one or more anchors such as sutures or screws.

Another Version of Example 1a

A penile prosthetic comprising: an expandable conduit; a pump; a reservoir; a first conduit that couples the expandable conduit to the pump; a second conduit that couples the reservoir to the pump; and a plate that couples to the expandable conduit, wherein the plate includes a concave surface; wherein: (a)(i) the expandable conduit has first and second opposing conduit ends; (a)(ii) the first conduit end is immediately adjacent to the plate; (a)(iii) the second conduit end includes a rounded tip; wherein: (b)(i) the first conduit has a side wall; (b)(ii) the side wall includes a thickness of between 0.1 and 0.5 mm; wherein the first conduit includes a maximum diameter of between 15 and 20 mm; wherein (c)(i) the plate includes a pliable portion; (c)(ii) the plate includes first and second opposing plate ends; (c)(iii) the first plate end is configured to rotate with respect to the second plate end; wherein: (d)(i) the plate includes first and second apertures; (d)(ii) the first aperture is adjacent the first plate end and the second aperture is adjacent the second plate end; (d)(iii) the first and second apertures are at least 3 cm from one another; (d)(iv) the plate has a maximum width of at least 3 cm.

Pliable, as used herein, means an object is supple enough to bend freely or repeatedly without breaking.

Example 2a

The prosthetic of example 1a comprising a resilient ellipse, wherein: the pump is resilient and includes an elliptical surface; the pump is not monolithic with the resilient ellipse.

Example 3a

The prosthetic of example 1a wherein: the malleable portion is included in a middle third of the plate; the middle third of the plate is between a first outer third of the plate and a second outer third of the plate.

The malleable portion may be malleable due to properties of a material included within plate. However, in other embodiments the malleable portion may be malleable due to the design of the plate. For example, in FIG. 4 the malleability or ability to shape the plate may be due to a weakened portion at distance 446 versus a wider distance 447.

Another Version of Example 3a

The prosthetic according to any of examples 1a-2a wherein: the malleable portion is included in a middle third of the plate; the middle third of the plate is between a first outer third of the plate and a second outer third of the plate.

Example 4a

The prosthetic of example 3a wherein: a first axis intersects the first and second plate ends; the plate includes third and fourth plate ends that oppose each other; a second axis intersects the third and fourth plate ends; the first axis is orthogonal to the second axis; the second axis intersects the middle third of the plate; a third axis intersects the third and fourth plate ends and the first outer third of the plate; the second axis is parallel to the third axis; the third and fourth plate ends are separated from each other by a first distance measured along the second axis; the third and fourth plate ends are separated from each other by a second distance measured along the third axis; the second distance is greater than the first distance.

Another Version of Example 4a

The prosthetic according to any of examples 1a-3a wherein: a first axis intersects the first and second plate ends; the plate includes third and fourth plate ends that oppose each other; a second axis intersects the third and fourth plate ends; the first axis is orthogonal to the second axis; the second axis intersects the middle third of the plate; a third axis intersects the third and fourth plate ends and the first outer third of the plate; the second axis is parallel to the third axis; the third and fourth plate ends are separated from each other by a first distance measured along the second axis; the third and fourth plate ends are separated from each other by a second distance measured along the third axis; the second distance is greater than the first distance.

Example 5a

The prosthetic of example 1a comprising an antibiotic on at least one of the expandable conduit, the pump, the plate, or the reservoir.

For instance, the antibiotic may be on some or all of the expandable conduit, the pump, the plate, or the reservoir.

Another Version of Example 5a

The prosthetic according to any of examples 1a-4a comprising an antibiotic on at least one of the expandable conduit, the pump, the plate, or the reservoir.

Example 6a

The prosthetic of example 5a comprising at least one of polytetrafluoroethylene, expanded polytetrafluoroethylene (ePTFE), polyethylene terephthalate (Dacron®), or polyurethane.

Another Version of Example 6a

The prosthetic according to any of examples 1a-5a comprising at least one of polytetrafluoroethylene, expanded polytetrafluoroethylene (ePTFE), polyethylene terephthalate (Dacron®), or polyurethane.

Example 7a

The prosthetic of example 6a comprising at least one of collagen, fibrin, or combinations thereof.

Another Version of Example 7a

The prosthetic according to any of examples 1a-6a comprising at least one of collagen, fibrin, or combinations thereof.

Example 8a

The prosthetic of example 1a comprising at least one of a foam, a hydrogel, or combinations thereof.

Another Version of Example 8a

The prosthetic according to any of examples 1a-7a comprising at least one of a foam, a hydrogel, or combinations thereof.

Example 9a

The prosthetic of example 1a comprising an additional expandable conduit, wherein the additional expandable conduit is coupled to the pump via at least one of the first conduit, a third conduit, or combinations thereof.

Another Version of Example 9a

The prosthetic according to any of examples 1a-8a comprising an additional expandable conduit, wherein the additional expandable conduit is coupled to the pump via at least one of the first conduit, a third conduit, or combinations thereof.

Example 10a

The prosthetic of example 1a wherein the pump comprises: a pump housing having a fluid passageway; first and second fluid ports in fluid communication with the fluid passageway and operatively connectable to the reservoir and the expandable conduit, respectively; a pump bulb, in fluid communication with the fluid passageway, which can be operated to transfer fluid between the first and second fluid ports through the fluid passageway; a first poppet positioned within the fluid passageway, the first poppet having an extending portion extending away from a body portion of the first poppet, the extending portion having a sealing surface biased toward a valve seat within the fluid passageway; a flange extending from a surface of the fluid passageway and toward an interior of the fluid passageway and spaced from the valve seat within the fluid passageway; and a fluid path between the extending portion of the first poppet and the flange when the extending portion of the first poppet is in contact with the flange, wherein the fluid path can allow fluid to pass from one side of the flange to the other.

Another Version of Example 10a

The prosthetic according to any of examples 1a-9a wherein the pump comprises: a pump housing having a fluid passageway; first and second fluid ports in fluid communication with the fluid passageway and operatively connectable to the reservoir and the expandable conduit, respectively; a pump bulb, in fluid communication with the fluid passageway, which can be operated to transfer fluid between the first and second fluid ports through the fluid passageway; a first poppet positioned within the fluid passageway, the first poppet having an extending portion extending away from a body portion of the first poppet, the extending portion having a sealing surface biased toward a valve seat within the fluid passageway; a flange extending from a surface of the fluid passageway and toward an interior of the fluid passageway and spaced from the valve seat within the fluid passageway; and a fluid path between the extending portion of the first poppet and the flange when the extending portion of the first poppet is in contact with the flange, wherein the fluid path can allow fluid to pass from one side of the flange to the other.

Example 11a

The prosthetic of example 10a, wherein: the pump comprises a second poppet; the first and second poppets are positioned within the fluid passageway and are aligned along a valve axis and biased toward first and second valve seats within the fluid passageway, respectively.

Example 12a

The prosthetic of example 11a, wherein the first poppet comprises an end slidingly engaged with an end of the second poppet.

Example 13a

The prosthetic of example 12a comprising a bypass chamber fluidly connected by a bypass input channel to the fluid passageway at a first location and fluidly connected by a bypass output channel to the fluid passageway at a second location, the bypass chamber comprising a bypass check valve biased toward a closed position along a check valve axis.

Example 14a

A penile prosthetic comprising: an inflatable conduit; a pump; a reservoir; a first conduit that couples the inflatable conduit to the pump and a second conduit that couples the reservoir to the pump; and a plate that couples to the inflatable conduit; wherein: (a)(i) the inflatable conduit has first and second opposing conduit ends; (a)(ii) the first conduit end is immediately adjacent to the plate; (a)(iii) the second conduit end includes a rounded tip; wherein: (b)(i) the first conduit has a side wall; (b)(ii) the side wall includes a thickness of between 0.1 and 0.5 mm; wherein the first conduit includes a maximum diameter of between 15 and 20 mm; wherein (c)(i) the plate includes a malleable portion; (c)(ii) the plate includes first and second opposing plate ends; wherein: (d)(i) the plate includes first and second apertures; (d)(ii) the first aperture is adjacent the first plate end and the second aperture is adjacent the second plate end; (d)(iii) the plate has a maximum width of at least 3 cm.

"Inflatable", as used herein, includes the introduction of a fluid (such as a liquid or gas) to fill an object.

Thus, some embodiments do not require a concave surface for the plate.

Example 15a

The prosthetic of example 14a wherein: a middle third of the plate includes the malleable portion; the middle third of the plate is between a first outer third of the plate and a second outer third of the plate.

Example 16a

The prosthetic of example 14a wherein: a first axis intersects the first and second plate ends; the plate includes third and fourth plate ends that oppose each other; a second axis intersects the third and fourth plate ends; the first axis is orthogonal to the second axis; the second axis intersects the middle third of the plate; a third axis intersects the third and fourth plate ends and the first outer third of the plate; the second axis is parallel to the third axis; the third and fourth plate ends are separated from each other by a first distance measured along the second axis; the third and fourth plate ends are separated from each other by a second distance measured along the third axis; the second distance is greater than the first distance.

Another Version of Example 16a

The prosthetic according to any of examples 14a-15a wherein: a first axis intersects the first and second plate ends; the plate includes third and fourth plate ends that oppose each other; a second axis intersects the third and fourth plate ends; the first axis is orthogonal to the second axis; the second axis intersects the middle third of the plate; a third axis intersects the third and fourth plate ends and the first outer third of the plate; the second axis is parallel to the third axis; the third and fourth plate ends are separated from each other by a first distance measured along the second axis; the third and fourth plate ends are separated from each other by a second distance measured along the third axis; the second distance is greater than the first distance.

Example 17a

The prosthetic of example 14a comprising an antibiotic on at least one of the inflatable conduit, the pump, the plate, or the reservoir.

Another Version of Example 17a

The prosthetic according to any of examples 14a-16a comprising an antibiotic on at least one of the inflatable conduit, the pump, the plate, or the reservoir.

Example 18a

The prosthetic of example 17a comprising at least one of polytetrafluoroethylene, expanded polytetrafluoroethylene (ePTFE), polyethylene terephthalate (Dacron®), or polyurethane.

Another Version of Example 18a

The prosthetic according to any of examples 14a-17a comprising at least one of polytetrafluoroethylene, expanded polytetrafluoroethylene (ePTFE), polyethylene terephthalate (Dacron®), or polyurethane.

Example 19a

A penile prosthetic comprising: an expandable conduit; a pump; a reservoir; a first conduit that couples the expandable conduit to the pump; a second conduit that couples the reservoir to the pump; and a plate that couples to the expandable conduit, wherein the plate includes a concave surface; an antibiotic on at least one of the expandable conduit, the pump, the plate, or the reservoir; wherein: (a)(i) the expandable conduit has first and second opposing conduit ends; (a)(ii) the first conduit end is immediately adjacent to the plate; (a)(iii) the second conduit end includes a rounded tip; wherein: (b)(i) the first conduit has a side wall; (b)(ii) the side wall includes a thickness of between 0.1 and 0.5 mm; wherein the first conduit includes a maximum diameter of between 15 and 20 mm; wherein: (c)(i) the plate includes first and second apertures; (c)(ii) the first aperture is adjacent the first plate end and the second aperture is adjacent the second plate end; (c)(iii) the first and second apertures are at least 3 cm from one another; (c)(iv) the plate has a maximum width of at least 3 cm.

Example 20a

The prosthetic of example 19a wherein: a first axis intersects the first and second plate ends; the plate includes third and fourth plate ends that oppose each other; a second axis intersects the third and fourth plate ends; the first axis is orthogonal to the second axis; the second axis intersects the middle third of the plate; a third axis intersects the third and fourth plate ends and the first outer third of the plate; the second axis is parallel to the third axis; the third and fourth plate ends are separated from each other by a first distance measured along the second axis; the third and fourth plate ends are separated from each other by a second distance measured along the third axis; the second distance is greater than the first distance.

The foregoing description of the embodiments of the invention has been presented for the purposes of illustration and description. It is not intended to be exhaustive or to limit the invention to the precise forms disclosed. This description and the claims following include terms, such as left, right, top, bottom, over, under, upper, lower, first, second, etc. that are used for descriptive purposes only and are not to be construed as limiting. For example, terms designating relative vertical position refer to a situation where a first side of a substrate is the "top" surface of that substrate; the substrate may actually be in any orientation so that a "top" side of a substrate may be lower than the "bottom" side in a standard terrestrial frame of reference and still fall within the meaning of the term "top." The term "on" as used herein (including in the claims) does not indicate that a first item "on" a second item is directly on and in immediate contact with the second item unless such is specifically stated; there may be a third item or other structure between the first item and the second item on the first item. The embodiments of a device or article described herein can be manufactured, used, or shipped in a number of positions and orientations. Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

What is claimed is:

1. A penile prosthetic comprising:
    an expandable conduit;
    a pump;
    a reservoir;
    a first conduit that couples the expandable conduit to the pump;
    a second conduit that couples the reservoir to the pump; and
    a plate that couples to the expandable conduit, wherein the plate includes a concave surface;
    wherein: (a)(i) the expandable conduit has first and second opposing conduit ends; (a)(ii) the first conduit end is immediately adjacent to the plate; (a)(iii) the second conduit end includes a rounded tip;
    wherein: (b)(i) the expandable conduit has a side wall; (b)(ii) the side wall includes a thickness of between 0.1 and 0.5 mm;
    wherein the expandable conduit includes a maximum diameter of between 15 and 20 mm;
    wherein (c)(i) the plate includes a malleable portion; (c)(ii) the plate includes first and second opposing plate ends; (c)(iii) the first plate end is configured to rotate with respect to the second plate end;
    wherein: (d)(i) the plate includes first and second apertures; (d)(ii) the first aperture is adjacent the first plate end and the second aperture is adjacent the second plate end; (d)(iii) the first and second apertures are at least 3 cm from one another; (d)(iv) the plate has a maximum width of at least 3 cm.

2. The prosthetic of claim 1 comprising a resilient ellipse, wherein:
the pump is resilient and includes an elliptical surface;
the pump is not monolithic with the resilient ellipse.

3. The prosthetic of claim 1 wherein:
the malleable portion is included in a middle third of the plate;
the middle third of the plate is between a first outer third of the plate and a second outer third of the plate.

4. The prosthetic of claim 3 wherein:
a first axis intersects the first and second plate ends;
the plate includes third and fourth plate ends that oppose each other;
a second axis intersects the third and fourth plate ends;
the first axis is orthogonal to the second axis;
the second axis intersects the middle third of the plate;
a third axis intersects the third and fourth plate ends and the first outer third of the plate;
the second axis is parallel to the third axis;
the third and fourth plate ends are separated from each other by a first distance measured along the second axis;
the third and fourth plate ends are separated from each other by a second distance measured along the third axis;
the second distance is greater than the first distance.

5. The prosthetic of claim 1 comprising an antibiotic on at least one of the expandable conduit, the pump, the plate, or the reservoir.

6. The prosthetic of claim 5 comprising at least one of polytetrafluoroethylene, expanded polytetrafluoroethylene (ePTFE), polyethylene terephthalate (Dacron®), or polyurethane.

7. The prosthetic of claim 6 comprising at least one of collagen, fibrin, or combinations thereof.

8. The prosthetic of claim 1 comprising at least one of a foam, a hydrogel, or combinations thereof.

9. The prosthetic of claim 1 comprising an additional expandable conduit, wherein the additional expandable conduit is coupled to the pump via at least one of the first conduit, a third conduit, or combinations thereof.

10. The prosthetic of claim 1 wherein the pump comprises:
a pump housing having a fluid passageway;
first and second fluid ports in fluid communication with the fluid passageway and operatively connectable to the reservoir and the expandable conduit, respectively;
a pump bulb, in fluid communication with the fluid passageway, which can be operated to transfer fluid between the first and second fluid ports through the fluid passageway;
a first poppet positioned within the fluid passageway, the first poppet having an extending portion extending away from a body portion of the first poppet, the extending portion having a sealing surface biased toward a valve seat within the fluid passageway;
a flange extending from a surface of the fluid passageway and toward an interior of the fluid passageway and spaced from the valve seat within the fluid passageway; and
a fluid path between the extending portion of the first poppet and the flange when the extending portion of the first poppet is in contact with the flange, wherein the fluid path can allow fluid to pass from one side of the flange to the other.

11. The prosthetic of claim 10, wherein:
the pump comprises a second poppet;
the first and second poppets are positioned within the fluid passageway and are aligned along a valve axis and biased toward first and second valve seats within the fluid passageway, respectively.

12. The prosthetic of claim 11, wherein the first poppet comprises an end slidingly engaged with an end of the second poppet.

13. The prosthetic of claim 12 comprising a bypass chamber fluidly connected by a bypass input channel to the fluid passageway at a first location and fluidly connected by a bypass output channel to the fluid passageway at a second location, the bypass chamber comprising a bypass check valve biased toward a closed position along a check valve axis.

14. A penile prosthetic comprising:
an inflatable conduit;
a pump;
a reservoir;
a first conduit that couples the inflatable conduit to the pump and a second conduit that couples the reservoir to the pump; and
a plate that couples to the inflatable conduit;
wherein: (a)(i) the inflatable conduit has first and second opposing conduit ends; (a)(ii) the first conduit end is immediately adjacent to the plate; (a)(iii) the second conduit end includes a rounded tip;
wherein: (b)(i) the inflatable conduit has a side wall; (b)(ii) the side wall includes a thickness of between 0.1 and 0.5 mm;
wherein the inflatable conduit includes a maximum diameter of between 15 and 20 mm;
wherein (c)(i) the plate includes a malleable portion; (c)(ii) the plate includes first and second opposing plate ends;
wherein: (d)(i) the plate includes first and second apertures; (d)(ii) the first aperture is adjacent the first plate end and the second aperture is adjacent the second plate end; (d)(iii) the plate has a maximum width of at least 3 cm.

15. The prosthetic of claim 14 wherein:
a middle third of the plate includes the malleable portion;
the middle third of the plate is between a first outer third of the plate and a second outer third of the plate.

16. The prosthetic of claim 14 wherein:
a first axis intersects the first and second plate ends;
the plate includes third and fourth plate ends that oppose each other;
a second axis intersects the third and fourth plate ends;
the first axis is orthogonal to the second axis;
the second axis intersects the middle third of the plate;
a third axis intersects the third and fourth plate ends and the first outer third of the plate;
the second axis is parallel to the third axis;
the third and fourth plate ends are separated from each other by a first distance measured along the second axis;
the third and fourth plate ends are separated from each other by a second distance measured along the third axis;
the second distance is greater than the first distance.

17. The prosthetic of claim 14 comprising an antibiotic on at least one of the inflatable conduit, the pump, the plate, or the reservoir.

18. The prosthetic of claim 17 comprising at least one of polytetrafluoroethylene, expanded polytetrafluoroethylene (ePTFE), polyethylene terephthalate (Dacron®), or polyurethane.

19. A penile prosthetic comprising:
an expandable conduit;
a pump;
a reservoir;
a first conduit that couples the expandable conduit to the pump;
a second conduit that couples the reservoir to the pump; and
a plate that couples to the expandable conduit, wherein the plate includes a concave surface;
an antibiotic on at least one of the expandable conduit, the pump, the plate, or the reservoir;
wherein: (a)(i) the expandable conduit has first and second opposing conduit ends; (a)(ii) the first conduit end is immediately adjacent to the plate; (a)(iii) the second conduit end includes a rounded tip;
wherein: (b)(i) the expandable conduit has a side wall; (b)(ii) the side wall includes a thickness of between 0.1 and 0.5 mm;
wherein the expandable conduit includes a maximum diameter of between 15 and 20 mm;
wherein: (c)(i) the plate includes first and second plate ends and first and second apertures; (c)(ii) the first aperture is adjacent the first plate end and the second aperture is adjacent the second plate end; (c)(iii) the first and second apertures are at least 3 cm from one another; (c)(iv) the plate has a maximum width of at least 3 cm.

20. The prosthetic of claim 19 wherein:
a first axis intersects the first and second plate ends;
the plate includes third and fourth plate ends that oppose each other;
a second axis intersects the third and fourth plate ends;
the first axis is orthogonal to the second axis;
the second axis intersects the middle third of the plate;
a third axis intersects the third and fourth plate ends and the first outer third of the plate;
the second axis is parallel to the third axis;
the third and fourth plate ends are separated from each other by a first distance measured along the second axis;
the third and fourth plate ends are separated from each other by a second distance measured along the third axis;
the second distance is greater than the first distance.

\* \* \* \* \*